United States Patent
Xiao

(10) Patent No.: US 9,744,206 B2
(45) Date of Patent: Aug. 29, 2017

(54) PHARMACEUTICAL COMPOSITIONS FOR TREATING CANCER OF GENITAL SYSTEM AND PREPARATION METHOD THEREFOR

(71) Applicant: Mingchun Xiao, Dongguan (CN)

(72) Inventor: Mingchun Xiao, Dongguan (CN)

( * ) Notice: Subject to any disclaimer, the term of this patent is extended or adjusted under 35 U.S.C. 154(b) by 99 days.

(21) Appl. No.: 14/745,517

(22) Filed: Jun. 22, 2015

(65) Prior Publication Data
US 2015/0283197 A1 Oct. 8, 2015

Related U.S. Application Data

(63) Continuation-in-part of application No. PCT/CN2013/084813, filed on Oct. 6, 2013.

(30) Foreign Application Priority Data

Mar. 11, 2013 (CN) .......................... 2013 1 0078199

(51) Int. Cl.

| | | |
|---|---|---|
| A61K 36/00 | (2006.01) |
| A61K 36/9068 | (2006.01) |
| A61K 36/752 | (2006.01) |
| A61K 36/804 | (2006.01) |
| A61K 36/85 | (2006.01) |
| A61K 36/884 | (2006.01) |
| A61K 36/888 | (2006.01) |
| A61K 36/8884 | (2006.01) |
| A61K 36/8888 | (2006.01) |
| A61K 36/8945 | (2006.01) |
| A61K 36/8988 | (2006.01) |
| A61K 36/8998 | (2006.01) |
| A61K 36/9062 | (2006.01) |
| A61K 36/9064 | (2006.01) |
| A61K 36/9066 | (2006.01) |
| A61K 36/46 | (2006.01) |
| A61K 36/481 | (2006.01) |
| A61K 36/484 | (2006.01) |
| A61K 36/53 | (2006.01) |
| A61K 36/54 | (2006.01) |
| A61K 36/575 | (2006.01) |
| A61K 36/68 | (2006.01) |
| A61K 36/71 | (2006.01) |
| A61K 36/714 | (2006.01) |
| A61K 36/734 | (2006.01) |
| A23F 3/16 | (2006.01) |
| A61K 36/076 | (2006.01) |
| A61K 36/232 | (2006.01) |
| A61K 36/233 | (2006.01) |
| A61K 36/284 | (2006.01) |
| A61K 36/48 | (2006.01) |
| A61K 36/482 | (2006.01) |
| A61K 36/532 | (2006.01) |
| A61K 36/535 | (2006.01) |
| A61K 36/538 | (2006.01) |
| A61K 36/539 | (2006.01) |
| A61K 36/65 | (2006.01) |
| A61K 36/66 | (2006.01) |
| A61K 36/88 | (2006.01) |
| A61K 36/8905 | (2006.01) |
| A61K 36/906 | (2006.01) |
| A61K 36/07 | (2006.01) |

(Continued)

(52) U.S. Cl.
CPC .......... *A61K 36/9068* (2013.01); *A23F 3/163* (2013.01); *A61K 36/07* (2013.01); *A61K 36/076* (2013.01); *A61K 36/12* (2013.01); *A61K 36/185* (2013.01); *A61K 36/21* (2013.01); *A61K 36/232* (2013.01); *A61K 36/233* (2013.01); *A61K 36/236* (2013.01); *A61K 36/237* (2013.01); *A61K 36/258* (2013.01); *A61K 36/268* (2013.01); *A61K 36/284* (2013.01); *A61K 36/46* (2013.01); *A61K 36/48* (2013.01); *A61K 36/481* (2013.01); *A61K 36/482* (2013.01); *A61K 36/484* (2013.01); *A61K 36/515* (2013.01); *A61K 36/53* (2013.01); *A61K 36/532* (2013.01); *A61K 36/535* (2013.01); *A61K 36/538* (2013.01); *A61K 36/539* (2013.01); *A61K 36/54* (2013.01); *A61K 36/575* (2013.01); *A61K 36/65* (2013.01); *A61K 36/66* (2013.01); *A61K 36/68* (2013.01); *A61K 36/71* (2013.01); *A61K 36/714* (2013.01); *A61K 36/734* (2013.01); *A61K 36/752* (2013.01); *A61K 36/804* (2013.01); *A61K 36/85* (2013.01); *A61K 36/88* (2013.01); *A61K 36/882* (2013.01); *A61K 36/884* (2013.01); *A61K 36/888* (2013.01); *A61K 36/8884* (2013.01); *A61K 36/8888* (2013.01); *A61K 36/8905* (2013.01); *A61K 36/8945* (2013.01); *A61K 36/8988* (2013.01); *A61K 36/8998* (2013.01); *A61K 36/906* (2013.01); *A61K 36/9062* (2013.01); *A61K 36/9064* (2013.01); *A61K 36/9066* (2013.01)

(58) Field of Classification Search
None
See application file for complete search history.

(56) References Cited

FOREIGN PATENT DOCUMENTS

| CN | 101190323 A | * | 6/2008 |
| CN | 101439171 A | * | 5/2009 |

* cited by examiner

*Primary Examiner* — Qiuwen Mi
(74) *Attorney, Agent, or Firm* — Wayne & Ken, LLC; Tony C. Hom

(57) ABSTRACT

A pharmaceutical composition for preventing and treating cancer of reproductive system and preparation method therefor. The pharmaceutical composition is prepared using one or more of the following as raw material: *pinellia* tuber, (Continued)

bighead *atractylodes rhizome, gastralia* tuber, liquorice root, Indian bread, white peony root, fresh ginger.

7 Claims, No Drawings

(51) Int. Cl.
*A61K 36/12* (2006.01)
*A61K 36/185* (2006.01)
*A61K 36/21* (2006.01)
*A61K 36/236* (2006.01)
*A61K 36/237* (2006.01)
*A61K 36/258* (2006.01)
*A61K 36/268* (2006.01)
*A61K 36/515* (2006.01)
*A61K 36/882* (2006.01)

PHARMACEUTICAL COMPOSITIONS FOR TREATING CANCER OF GENITAL SYSTEM AND PREPARATION METHOD THEREFOR

CROSS-REFERENCE TO RELATED APPLICATIONS

This application is a continuation-in-part of International Patent Application No. PCT/CN2013/084813 with an international filing date of Oct. 6, 2013, designating the United States, and further claims priority benefits to Chinese Patent Application No. 201310078199.5 filed Mar. 11, 2013. The contents of all of the aforementioned applications, including any intervening amendments thereto, are incorporated herein by reference.

TECHNICAL FIELD

The present invention, belonging to the medical care field, is a pharmaceutical composition for treating cancer of genital system. It is applicable to diseases of genital system, such as proliferation of mammary glands, breast cancer, liver lithiasis, cirrhosis, liver cancer, uterine fibroids, endometrial cancer, ovarian cancer, benign prostatic hyperplasia, and prostatic cancer. Besides, it can prevent and treat gastric ulcer and gastric cancer. The present invention is a pharmaceutical composition for treating and preventing cancer of genital system and preparation method therefor.

BACKGROUND OF THE INVENTION

Cancer is the primary cause of death in humans. It is estimated by World Health Organization that there will be 84 million people died of cancer the period from 2005 to 2015 if no intervention. Deaths from cancer amounted to 7.4 million (about 13% of all deaths). Over 70% cancer deaths happen in low income countries and middle income countries. Deaths from cancer worldwide are projected to continue to rise to 12 million in 2030.

Up to now, the effect of chemotherapy and radiotherapy is not obvious, and there are some defects such as toxic side effects, patients strong react after treatment, and a high degree of pain. Early surgical treatment is easily to recur and metastasize and the effect is also not obvious.

SUMMARY OF THE INVENTION

A technical problem to be solved by the present invention is to overcome above deficiencies of method for treating cancer by means of a pharmaceutical composition for treating cancer of genital system of a significant effect, low cost, low toxicity.

In the process of studying theory Traditional Chinese Medicine (TCM), analysis of *Headache* in *Famous Doctors Medical Record Analysis of Past Dynasties* by Zhang Yuansu from Jin dynasty was found. The conclusion that Jueyin disease is lung cancer combined with brain tumor and Taiyin disease is liver cancer has been made, as Zhang said, through careful discrimination about "Jueyin and Taiyin diseases are called wind-phlegm headache" in *Headache* and logical deduction of "Jueyin liver meridian of foot and spleen meridian of foot-taiyin, applying TCM theory. So "wind-phlegm headache" is the lung cancer combined with brain tumors accompanying liver metastasis. Combined with *Yuhu Pill* treating the disease by Zhang, I found *Decoction of Pinellia Ternata, Gastrodia Elata Bl, and Atractylodes Macrocephala* (Composition: *Pinellia ternata, Gastrodia elata* Bl, *Atractylodes macrocephala, Poria cocos,* tangerine peel, licorice, ginger) is a basic prescription of treating systemic cancer. Besides, I found the "Fungus" is one of major factors of cancer through further analysis, and the canceration of genital system is mainly resulting from *candida albicans*.

According to TCM theory, the genital system is mainly attributable to the liver meridian, and subordinate to spleen meridian and kidney meridian. Modern medicine has proved that the establishment of normal female menstrual cycle depends on the neuroendocrine regulation of hypothalamic-pituitary-ovarian axis, and the endometrialcyclic response to hormonal changes, the liver plays a regulating rule on sex hormone. I also have found that the liver meridian mainly reflects brain lesions previously, while spleen meridian mainly reflects the liver and spleen lesions. TCM treatment principle of genital system disease is "soothing the liver and strengthening the spleen", which means blood vessels negotiation, nutrition supplements; elimination of edema, and enhancing function of liver, spleen, pancreas and other internal organs. *Xiaoyao Pill* is the representative work (composition: licorice, *angelica sinensis, Poria cocas,* white paeony root, *atractylocles macrocephala, bupleurum*), which was mainly used for early stage mammary gland proliferation, irregular menstruation and other diseases. The *angelica sinensis* and white paeony root are used for promoting blood circulation of liver and spleen to enrich blood and promote blood flow; the *atractylodes macrocephala* and *poria cocos* are used for eliminating edema in liver and spleen cells, the *atractylodes macrocephala* chemical constituents of volatile oil plays an inhibit role on mould; while *bupleurum* is used for virus infection in liver blood; licorice, as an adjuvant drug, can only play a part of harmony. From the role of six medicines to analyze, the weak effectiveness results in therapeutic effect can not achieved. And "*Bupleurum*" is mainly used in the treatment of viral infection; it is not allowed to be used when "liver wind agitation", namely canceration happened.

*Pinellia ternate* and *gastrodia elata* Bl are monarch drugs in the treatment of systemic cancer in *Prescription of TCM treatment of Lung Cancer with Brain Tumor with Liver Cancer Metabasis*. Therefore, *Pinellia ternate* and *gastrodia elata* Bl are still monarch drugs in the treatment of cancer in genital system; the difference with the metabasis is the treatment focus. The metabasis focuses on the brain treatment, while the cancer of genital system focuses on liver treatment. Because the liver meridian is from hepatic portal vein, which is easily to be obstructed and cause portal hypertension, resulting in many varicose veins when it is infected by mould and virus. With the further violation of mould, the anastomosis between the portal vein and vena cava gradually expand to formulate collateral circulation to let the portal blood into the vena cave through collateral circulation to the heart. The main collateral circulations include: 1. Varices of lower esophagus and gastric coronary, which is the reason of gastrointestinal hemorrhage. 2. Abdominal wall and paraumbilical vein. 3. Haemorrhoidal vein, which is the reason of haemorrhoidal bleeding. Meanwhile, as the process of portal vein obstruction, it also results in liver lithiasis, liver cirrhosis, and liver malfunction, causing metabolic abnormity, mainly reducing the liver inactivation of estrogen, which affects the function of entire genital system. This is why women face appears stain, as normal liver function has ability to inactivate estrogen and increase progesterone content. Therefore, the principle of treating and preventing diseases of genital system is mainly to promote the portal vein blood circulation, so it is necessary to strengthen the use of drugs for invigorating blood circulation and eliminating stasis.

Monarch, minister, assistant and guide compatibility principle is paid attention to in TCM prescription, but also the use of "guiding drugs", which is equivalent to targeting effects. Therefore, in the treatment of the genital system, *Decoction of Pinellia Ternata, Gastrodia Elata Bl, and Atractylodes Macrocephala* is monarch drug, and minister drug is replaced by *Xiaoyao Pill*, while the assistant drug is to strengthen drugs for invigorating blood circulation and eliminating stasis.

The main pathways of mould invasion into liver are: chill cold metastasis, food-borne infection, sexually-transmitted infection, mother-to-child transmission, transfusion infection and other infections. It is very important to treat chill cold actively. Currently using antiallergic drugs when treating chill cold is wrong, because it inhibits sneezing, so the mold will not be eliminated with nasal discharge and sputum, but transfer to the brain and liver. Therefore, to prevent canceration of the genital system, the first is to resist chill cold. The drug is also *Decoction of Pinellia Ternata, Gastrodia Elata Bl, and Atractylodes Macrocephala* combined with *Decoction of Bupleurum* and *Xiaoyao Pill*. Actually, *Decoction of Bupleurum* and *Xiaoyao Pill* is divided into two prescriptions as a prescription. With the addition of wind-cold-effusing medicinal like "*radix sileris, herba schizonepetae, perilla*", the prescription becomes *Pinellia ternata, Atractylodes macrocephala, Gastrodia elata* Bl, licorice, *Poria cocos*, white paeony root, tangerine peel, ginger, *radix sileris, herba schizonepetae, perilla, bupleurum, radix scutellariae*.

After the mould invasion into liver, blood circulation of liver should be accelerated to prevent mould reproducing. In the drugs for invigorating blood circulation and eliminating stasis, "*rhizome corydalis*" is the foremost drug with the property of acrid, bitter, and warm. It can treat all pains throughout the body. The chemical constituents mainly contain multiple alkaloids, which can inhibit and kill mold, as well as disperse the clustered mould in the blood and eliminate it with the blood to open blood vessels. Pain eliminate naturally if the blood is circulated. The *rhizoma corydalis* is often associated with *rhizome cyperi* for synergistic effect. The *rhizoma cyperi* belongs to qi-regulating drug, which means it can help the exchange between oxygen and carbon dioxide in the blood and promote the elimination of carbon dioxide. So drugs for invigorating blood circulation and eliminating stasis and di-regulating drugs will be used simultaneously to activate vital energy and blood. With volatile oil and alkaloids in chemical constituents, the *rhizoma cyperi* can inhibit mould and virus.

The "*radix curcumae*" is a kind of drug for invigorating blood circulation and eliminating stasis targeted for liver with the property of acrid, bitter, and warm. Its chemical constituents contain multiple volatile oils, which can inhibit mould, virus and bacillus. The *radix curcumae* is often associated with the qi-regulating drugs "costustoot", which is warm-natured and can complement the cold nature of *radix curcumae*. And the chemical constituents of costustoot also contain volatile oil and alkaloid.

The hepatotoxin is mainly eliminated through excrement and urine, and women may also be discharged through menstrual blood. Therefore, we should associate with drugs used for kidney meridian. The early symptoms are mild, so the *Decoction of Poria Cocos, Cassia Twig, Atractylodes Macrocephala and Licorice*, (Composition: *poria cocos, cassia* twig, *atractylodes macrocephala*, licorice) can be used, which is a partial prescription of *Decoction of Pinellia Ternata, Gastrodia Elata Bl, and Atractylodes Macrocephala*, but the *cassia* twig is added. Besides, the "*desmodium*" and dampness-transforming medicinal "*agastache rugosus* and *mangnolia officinalis*" should be added because mould to hepatic pathological change in early stage is microlithiasis. So combined *Decoction of Pinellia Ternata, Gastrodia Elata Bl, and Atractylodes Macrocephala* with *Decoction of Poria Cocos, Cassia Twig, Atractylodes Macrocephala and Licorice*, pharmaceutical composition for treating early cancer of genital system is: *pinellia ternata, gastrodia elata* Bl, *atractylodes macrocephala, rhizoma corydatis, rhizoma cyperi*, costustoot, licorice, *poria cocos, angelica sinensis*, white paeony root, *radix curcumae*, tangerine peel, *cassia* twig, *desmodium*, ginger, *agastache rugosus, mangnolia officinalis*.

With further development of the disease, drugs for nourishing qi and enriching blood should be added when liver function and spleen function begin to decrease and bloating, obesity, menorrhagia, menostaxis and other symptoms happened. TCM consider excessive menstrual blood is due to spleen deficiency, which means spleen does not govern the blood. In drugs for nourishing qi, "*radix scutellariae*" is the foremost, and it can enhance mutual curative effect with "*radix codonopsis*". Except *angelica sinensis*, another drug for enriching the blood like "*radix rehmanniae preparata*" should be added. Meanwhile, add "*rhizoma atractylodis*" and "*radix sileris*" to enhance the efficacy for treating "damp evil"; besides, change "*cassia* twig" into "cinnamon", remove "*radix curcumae.*". "*desmodium*" and add the "*Yam Rhizome*". Then the third pharmaceutical composition become: *ternata, gastrodia elata* Bl, *atractylodes macrocephafa, rhizoma corydalis, rhizoma cyperi*, costustoot, licorice, *poria cocos, angelica sinensis*, white paeony root, *radix curcumae*, tangerine peel, cinnamon, ginger, *radix scutellariae, radix codonopsis, radix rehmanniae preparata, agastache rugosus, rhizoma atractyloclis, mangnolia officinalis, radix sileris, Yam Rhizome*.

Then with further decrease of liver function and kidney function, which means deficiency syndrome is transferred into sthenia syndrome as TCM said, symptoms such as scant menstrual flow, proliferation of mammary glands, uterine fibroids, prostatic hyperplasia, upset and insomnia, dry mouth, chromatosis, back ache and leg cold will show. In this case, drugs for symptoms should be strengthened. In drugs for promoting blood circulation and regulating menstruation, "*caulis spatholobi*" can regulate painful menstruation, enrich the blood and warm lumbar kidney. Besides, add the drug of breaking blood stasis and easing pain like "*rhizoma curcumae*" and "*rhizoma sparganii*" and change the "cinnamon" into "monkshood" strengthen antifungal effect. And remove *agastache rugosus*, tangerine peel and add "*fructus aurantii immaturus*". The main chemical constituent of "*rhizoma sparganii*" is volatile oil, which has an effect on mould, virus and bacillus. Then the fourth pharmaceutical composition becomes: *pinellia ternata, gastrodia elata* Bl, *atractylodes macrocephala, rhizoma corydalis, rhizoma cyperi*, costustoot, licorice, *poria cocos, angelica sinensis*, white paeony root, *fructus aurantii irnmaturus*, monkshood, ginger, *radix scutellariae, radix codonopsis, radix rehmanniae preparata, rhizoma atractylodis, mangnolia officinalis, radix sileris, Yam rhizome, caulis spatholobi, rhizoma curcumae, rhizorra sparganii*.

With further decrease of liver, spleen, kidney and other organs function, which means deficiency of liver-yin and kidney-yin as TCM said, clinic symptoms like edema, diabetes will show, so does the heel pain. And the condition has been developed into mid-term, at this time the treatment of kidney should be strengthened by means of adding drugs for diuresis detumescence like "*rhizoma alismatis* and *polyporus*", changing *rhizome curcumae* and *rhizoma sparganii* into "*radix achyranthis bidentatae*", changing *radix codonopsis* into "ginseng" to restore kidney function and adding antirheumatic like "*angelica pubescens, herba taxilli* and *asarum*". So the fifth pharmaceutical composition is *pinellia ternata, gastrodia elata* Bl, *atractylodes macrocephala, rhizoma corydalis, rhizome cyperi,* costustoot, licorice, *poria cocos, angelica sinensis,* white paeony root, *fructus aurantii immaturus* monkshood, ginger, *radix scutellariae,* ginseng (*radix rehmanniae preparata, rhizoma atractylodis, mangnolia officinalis, radix sileris,* Yam rhizome, *caulis spatholobi, radix achyranthis bidentatae, rhizome alismatis,* polyporus, *angelica pubescens, herba taxilli,* and *asarum.*

When the early cancer of genital system combined with high blood pressure, it is time to add drugs for opening blood vessels in the brain like "*ligusticum wallichii* and *radix angelicae dahuricae*" and remove *radix scutellariae,* ginseng, *radix rehmariniae preparata,* monkshood and polyporus. So the sixth pharmaceutical composition is: *pinellia ternata, gastrodia elata* Bl, *atractylodes macrocephala, rhizoma corydalis, rhizome cyperi,* costustoot, licorice, *poria cocas, angelica sinensis,* white paeony root, *fructus aurantil immaturus,* ginger, *rhizome atractylodis, mangnolia officinalis, radix sileris,* Yam rhizome, *caulis spatholobi, radix achyranthis bidentatae, rhizoma alismatis, polyporus, angelica pubescens, herba taxilli, asarum, ligusticum wallichii* and *radix angelicae dahuricae. Ligusticum wallichii* and *radix angelicae dahuricae* have an targeting effect on high blood pressure caused by liver meridian, and *caulis spatholobi, angelica pubescens, herba taxilli* and *asarum* have an targeting effect on kidney meridian. Based on my clinical experience, brain venous disease caused by liver meridian lies on left prefrontal cortex, toxin of which is eliminated through left-side nasal cavity; while brain venous disease caused by kidney meridian lies on brain occiput, toxin of which is eliminated through right-side nasal cavity.

With further development of the disease, the illness has reached an advanced stage. At this time headache and multiple pains throughout the body will show, which means the combined disease of liver meridian, spleen meridian and kidney meridian as TCM said. Now it is time to increase the treatment of brain, lung expectorant and anti-rheumatic drugs, drugs for diuresis detumescence.

TCM consider that treating disease should regard "medication and diet therapy" as equal importance. So TCM attach importance to diet therapy, a reasonable diet can play a role of adjuvant therapy when taking medicine. TCM pay stress on cooking soup, which means using chicken, pig, sheep, cattle and other animals, bones and all, with onion, ginger, garlic, pepper, wild pepper, anise, cinnamon, cumin, bay leaves, amomum tsao-ko, cloves and other spices to boil together. These spices have effects on inhibiting mould, virus and bacillus and bones replenish the nutrition human needed to reinforce Qi and enrich blood, accordingly, the human body resistance can be enhanced, especially the efficacy of beef and ox bone is equal to *radix scutellariae.*

One. Differences Between the Present Invention and PCT/CN2013/080936 International Patent.

1. Different focus of treatment: the treatment of PCT/CN2013/080936 patent focuses on brain, and liver and kidney are next. Drugs, the principle of which is to promote the elimination of sputum and nasal discharge, are mainly for headache. So its monarch drugs are the combination of *Yuhu Pill* and *Pingwei Powder* adding guiding drugs like *radix angelicas dahuricae* and *ligusticum wallichii.* Minister drugs comprise *The Medicinal Broth of Incised Notopterygium Rhizome or Root Dewetting* and *Duhuo Jisheng Decoction,* aiming at strengthening the role of relieving pain and expelling wind-damp. And assistant drugs are drugs for diuresis detumescence. While the present invention focuses on liver, and kidney and brain are next. Mould intrudes the whole body with the blood circulation, so TCM has a focus based on the systematic therapy. Consequently, the composition of the present invention is to consider *Decoction of Pinellia Ternata, Gastrodia Elata Bl, and Atractylodes Mactocephala* as monarch drug, *Xiaoyao Pill* as minister drug and drugs for promoting circulation and removing stasis enhancement as assistant drugs. The medication principles are to open the blood circulation of liver.

2. Different pathological stage in the treatment: Patent PCT/CN2013/080936 is used for middle and terminal cancer, when headache and multiple pains throughout the body often happened. At this time, the kidney function is impaired heavily and edema is obvious. So in the assistant drugs, multiple drugs for diuresis detumescence should be combined. And the present invention is used for preventing cancer and treating early and middle stages cancer. So it can be also used for high blood pressure, hyperlipemia, diabetes and other precancerous lesions. Besides, it can remove stain and lose weight.

Two. Pharmaceutical Composition Preparation Methods

1. Prescription for preventing cancer of genital system: 0~50 dosages of *pinellia ternate,* 0~50 dosages of *atractylodes macrocephala,* 0~50 dosages of *gastrodia elata* Bl, 0~50 dosages of licorice, 0~50 dosages of *poria cocos,* 0~50 dosages of white paeony root, 0~50 dosages of tangerine peel, 0~50 dosages of ginger, 0~50 dosages of *radix sileris,* 0~50 dosages of *herba schizonepetae,* 0~50 dosages of *perilla,* 0~50 dosages of *bupieurum* and 0~50 dosages of *radix scutellariae.*

2. Add and subtract the prescription based on Method One, so the prescription for treating early stage cancer of genital system is: 0~50 dosages of *pinellia ternate,* 0~50 dosages of *atractylodes macrocephala,* 0~50 dosages of *gastrodia elata* Bl, 0~50 dosages of *rhizoma corydalis,* 0~50 dosages of *rhizoma cyperi,* 0~50 dosages of costustoot, 0~50 dosages of licorice, 0~50 dosages of *angelica sinensis,* 0~50 dosages of *poria cocas,* 0~50 dosages of white paeony root, 0~50 dosages of *radix curcumae,* 0~50 dosages of tangerine peel, 0~50 dosages of *cassia* twig, 0~50 dosages of *desmodium,* 0~50 dosages of ginger, 0~50 dosages of *agastache rugosus,* and 0~50 dosages of *mangnolia officinalis.*

3. Based on Method Two, add and subtract crude drugs to comprise the prescription when menorrhagia appeared: 0~50 dosages of *pinellia ternate,* 0~50 dosages of *atractylodes macrocephala,* 0~50 dosages of *gastrodia elata* Bl, 0~50 dosages of *rhizoma corydalis,* 0~50 dosages of *rhizoma cyperi,* 0~50 dosages of costustoot, 0~50 dosages of licorice, 0~50 dosages of *angelica sinensis,* 0~50 dosages of *poria cocos,* 0~50 dosages of white paeony root, 0~50 dosages of tangerine peel, 0~50 dosages of cinnamon, 0~50 dosages of ginger, 0~50 dosages of *radix scutellariae,* 0~50 dosages of *radix codonopsis,* 0~50 dosages of *radix rehmanniae preparata,* 0~50 dosages of *agastache rugosus,* 0~50 dosages of *rhizoma atractylodis,* 0~50 dosages of *mangnolia officinalis,* 0~50 dosages of *radix sileris* and 0~50 dosages of Yam Rhizome 4. Based on Method Three, add and subtract crude drugs to comprise the prescription when edema appeared: 0~50 dosages of *pinellia ternate,* 0~50 dosages of *atractylodes macrocephaia,* 0~50 dosages of *gastrodia elata* Bl, 0~50 dosages of *rhizoma corydalis*, 0~50 dosages of *rhizoma cyperi*, 0~50 dosages of costustoot, 0~50 dosages of licorice, 0~50 dosages of *angelica sinensis*, 0~50 dosages of *poria cocas*, 0~50 dosages of white paeony root, 0~50 dosages of *fructus aurantii immaturus*, 0~50 dosages of monkshood, 0~50 dosages of ginger. 0~50 dosages of *radix scutellariae*, 0~50 dosages of *radix codonopsis*, 0~50 dosages of *radix rehmanniae preparata*, 0~50 dosages of *rhizoma atractylodis*, 0~50 dosages of *mangnolia officinalis*, 0~50 dosages of *radix sileris*, 0~50 dosages of Yam Rhizome, 0~50 dosages of *caulis spatholobi*, 0~50 dosages of *rhizoma curcumae*, and 0~50 dosages of *rhizoma sparganii*.

5. Based on Method Four, add and subtract crude drugs to comprise the prescription when edema, heel pain and diabetes appeared: 0~50 dosages of *pinellia ternata*, 0~50 dosages of *gastrodia elata* Bl, 0~50 dosages of *atractylodes macrocephala*, 0~50 dosages of *rhizoma corydalis*, 0~50 dosages of *rhizoma cyperi*, 0~50 dosages of costustoot, 0~50 dosages of licorice, 0~50 dosages of *poria cocas*, 0~50 dosages of *angelica sinensis*, 0~50 dosages of white paeony root, 0~50 dosages of *fructus aurantii immaturus*, 0~50 dosages of monkshood, 0~50 dosages of ginger, 0~50 dosages of *radix scutellariae*, 0~50 dosages of ginseng, 0~50 dosages of *radix rehmanniae preparata*, 0~50 dosages of *rhizoma atractylodis*, 0~50 dosages of *mangnolia officinalis*, 0~50 dosages of *radix sileris*, 0~50 dosages Yam rhizome, 0~50 dosages *caulis spatholobi*, 0~50 dosages of *radix achyranthis bidentatae*, 0~50 dosages of *rhizoma alismatis*, 0~50 dosages of polyporus, 0~50 dosages of *angelica pubescens*, 0~50 dosages of *herba taxilli*, and 0~50 dosages of *asarum*.

6. Based on Method Five, add and subtract crude drugs to comprise the prescription when early stage cancer of genital system combined with the high blood pressure: 0~50 dosages of *pinellia ternata*, 0~50 dosages of *gastrodia elata* Bl, 0~50 dosages of *atractylodes macrocephala*, 0~50 dosages of *rhizoma corydalis*, 0~50 dosages of *rhizoma cyperi*, 0~50 dosages of costustoot, 0~50 dosages of licorice, 0~50 dosages of *poria cocas*, 0~50 dosages of *angelica sinensis*, 0~50 dosages of white paeony root, 0~50 dosages of *fructus aurantii immaturus*, 0~50 dosages of ginger, 0~50 dosages of *rhizoma atractylodis*, 0~50 dosages of *mangnolia officinalis*, 0~50 dosages of *radix sileris*, 0~50 dosages of Yam rhizome, 0~50 dosages of *caulis spatholobi*, 0~50 dosages of *radix achyranthis bidentatae*, 0~50 dosages of *rhizoma alismatis*, 0~50 dosages of polyporus, 0~50 dosages of *angelica pubescens*, 0~50 dosages of *herba taxilli*, 0~50 dosages of *asarum*, 0~50 dosages of *ligusticum wallichii* and 0~50 dosages of *radix angelicae dahuricae*.

The above six pharmaceutical compositions of the present invention add various conventional auxiliary materials as different dosage forms needed like disintegrants, lubricants and adhesives to prepare any kind of oral preparations, including pills, capsules, tablets, granules or oral liquids, syrup and other dosage forms. It can prepare pieces of Chinese medicine directly to make health tea.

Besides, the above six pharmaceutical compositions of the present invention can extract effective chemical composition such as alkaloid, volatile oil and other powerful chemicals from crude drug to prepare biological agents, including oral preparation (like capsules, tablets, granules or oral liquids), injection (including various doses) and drugs for external use (including health products).

The above six pharmaceutical compositions of the present invention can be prepared into different doses based on different age and differentiation between men and women.

The above pharmaceutical compositions of the present invention are applicable to medical drugs, health food, health products, animal drugs, and animal feed.

Following are advantages of the present invention:
1. Compliance with national formulary.
2. Convenient to use and safety.
3. Accurate curative effect and scarce side-effects,
4. Easy to get crude drugs and easy to generalize.
5. Mature, simple and cheap production process of Chinese patent medicine.
6. Mature raw material extraction technique of biological agents.
7. Clinical human trial over 2,000 years from Qin dynasty to now proved the accurate curative effect,
8. Compared with synthetic chemicals, the present invention has efficacy of killing mould, dissolving mould cluster and eliminating it out of the body. And it can recover liver and kidney function.

MAJOR STRUCTURE OF PATENT PROTECTION

1~50 dosages of *pinelli aternate*, 1~50 dosages of *atractylodes macrocephala*, 1~50 dosages of *gastrodia elata* Bl, 1~50 dosages of licorice, 1~50 dosages of *poria cocas*, and 1~50 dosages of *fructus aurantii immaturus*.

1~50 dosages of *pinelli aternate*, 1~50 dosages of *atractylodes macrocephala*, 0~51 dosages of *gastrodia elata* Bl, 1~50 dosages of licorice, 0~50 dosages of *poria cocas*, 0~50 dosages of white paeony root, 0~50 dosages of tangerine peel, 0~50 dosages of ginger, 1~50 dosages of *radix sileris*, 1~50 dosages of *herba schizonepetae*, 0~50 dosages of perilla, 0~50 dosages of bupleurum and 0~50 dosages of *radix scutellariae*.

1~50 dosages of *pinelli aternate*, 1450 dosages of *atractylodes macrocephala*, 1~50 dosages of *gastrodia elata* Bl, 1~50 dosages of *rhizoma coryclalis*, 1~50 dosages of *rhizoma cyperi*, 1~50 dosages of costustoot, 1~50 dosages of licorice, 1~50 dosages of *angelica sinensis*, 1~50 dosages of *poria cocos*, 1~50 dosages of white paeony root, 0~50 dosages of *radix curcumae*, 0~50 dosages of tangerine peel, 0~50 dosages of *cassia* twig, 0~50 dosages of *desmodium*, 0~50 dosages of ginger, 0~50 dosages of *agastache rugosus*, and 0~50 dosages of *mangnolia officinalis*.

1~50 dosages of *pinelliaternate*, 1~50 dosages of *atractylodes macrocephala*, 1~50 dosages of *gastrodia elata* Bl, 0~50 dosages of *rhizoma corydalis*, 0~50 dosages of *rhizoma cyperi*, 0~50 dosages of costustoot, 1~50 dosages of licorice, 0~50 dosages of *angelica sinensis*, 0~50 dosages of *poria cocos*, 0~50 dosages of white paeony root, 0~50 dosages of tangerine peel, 1~50 dosages of cinnamon, 1~50 dosages of ginger, 1~50 dosages of *radix scutellariae*, 1~50 dosages of *radix codonopsis*, 0~50 dosages of *radix rehmanniae preparata*, 0~50 dosages of *agastache rugosus*, 1~50 dosages of *rhizoma atractylodis*, 1~50 dosages of *mangnolia officinalis*, 0~50 dosages of *radix sileris* and 0~50 dosages of Yam Rhizome.

1~50 dosages of *pinelliaternate*, 1~50 dosages of *atractylodes macrocephala*, 1~50 dosages of *gastrodia elata* Bl, 1~50 dosages of *rhizoma corydalis*, 1~50 dosages of *rhizoma cyperi*, 1~50 dosages of costustoot, 1~50 dosages of licorice, 0~50 dosages of *angelica sinensis*, 0~50 dosages of *poria cocos*, 0~50 dosages of white paeony root, 0~50 dosages of *fructus aurantii immaturus*, 0~50 dosages of monkshood, 0~50 dosages of ginger, 0~50 dosages of *radix scutellanae*, 0~50 dosages of *radix codonopsis*, 0~50 dosages of *radix rehmanniae preparata*, 0~50 dosages of *rhi-* zoma atractylodis, 0~50 dosages of mangnolia officinalis, 0~50 dosages of radix sileris, 0~50 dosages of Yam Rhizome, 0~50 dosages of caulis spatholobi, 1~50 dosages of rhizoma curcumae, and 1~50 dosages of rhizoma sparganii.

1~50 dosages of pinellia ternata, 1~50 dosages of gastrodia elata Bl, 1~50 dosages of atractylodes macrocephala, 1~50 dosages of rhizoma corydalis, 1~50 dosages of rhizoma cyperi, 0~50 dosages of costustoot, 1~50 dosages of licorice, 0~50 dosages of poria cocos, 1~50 dosages of angelica sinensis, 0~50 dosages of white paeony root, 0~50 dosages of fructus aurantii immaturus, 1~50 dosages of monkshood, 1~50 dosages of ginger, 1~50 dosages of radix scutellariae, 0~50 dosages of ginseng, 0~50 dosages of radix rehmanniae preparata, 1~50 dosages of rhizoma atractylodis, 1~50 dosages of mangnolia officinals, 0~50 dosages of radix sileris, 0~50 dosages Yam rhizome, 0~50 dosages caulis spatholobi, 1~50 dosages of radix achyranthis bidentatae, 1~50 dosages of rhizoma alismatis, 1~50 dosages of polyporus, 1~50 dosages of angelica pubescens, 0~50 dosages of herba taxilli, and 1~50 dosages of asarum.

1~50 dosages of pinellia ternata, 1~50 dosages of gastrodia elata Bl, 1~50 dosages of atractylodes macrocephala, 0~50 dosages of rhizoma corydalis, 0~50 dosages of rhizoma cyperi, 0~50 dosages of costustoot, 1~50 dosages of licorice, 0~50 dosages of poria cocos, 0~50 dosages of angelica sinensis, 1~50 dosages of white paeony root, 1~50 dosages of fructus aurantil immaturus, 0~50 dosages of ginger, 0~50 dosages of rhizoma atractylodis, 0~50 dosages of mangnolia officinalis, 0~50 dosages of radix sileris, 0~50 dosages of Yam rhizome, 1~50 dosages of caulis spatholobi, 1~50 dosages of radix achyranthis bidentatae, 0~50 dosages of rhizoma alismatis, 0~50 dosages of polyporus, 0~50 dosages of angelica pubescens, 0~50 dosages of herba taxilli, 0~50 dosages of asarum, 1~50 dosages of ligusticum wallichii and 1~50 dosages of radix angelicae dahuricae.

REFERENCES

1. Deng Zhongjia, National Advanced Planned Textbook for TCM Colleges and Universities, *Prescription*, Chinese Traditional Medicine Press. September 2009
2. Gao Xuernin, National Advanced Planned Textbook for TCM Colleges and Universities, *Traditional Chinese Pharmacology*, Chinese Traditional Medicine Press. September 2009
3. Yi Fayin, Hu Fanglin, *Famous Doctors Medical Record Analysis of Past Dynasties*, Medical Publishing Bureau of Chemical Industry Press. April 2008.
4. He Ruizni, *Pathology, People's Medical Publishing House. (fourth edition)*, May 2001.

I claim:

1. A pharmaceutical composition for treating cancer of genital system caused by fungus, bacillus, virus and other anaerobic bacteria, characterized in that it comprises crude drugs of following weight:

1-50 dosages of pinellia ternate;
   1-50 dosages of atractylodes macrocephala;
   1-50 dosages of gastrodia eleta,
   1-50 dosages of licorice,
   1-50 dosages of poria cocos,
   1-50 dosages of fructus aurantii immaturus;
   0-50 dosages of white paeony root;
   0-50 dosages of tangerine peel;
   0-50 dosages of ginger;
   1-50 dosages of radix sileris;
   1-50 dosages of herba schizonepetae;
   0-50 dosages of perilla;
   0-50 dosages of bupleurum; and
   0-50 dosages of radix scutellariae.

2. The pharmaceutical composition of claim 1, further comprising:
   1-50 dosages of rhizoma corydalis;
   1-50 dosages of rhizoma cyperi;
   1-50 dosages of costustoot;
   1-50 dosages of angelica sinensis;
   0-50 dosages of radix curcumae;
   0-50 dosages of cassia twig;
   0-50 dosages of desmodium;
   0-50 dosages of agastache rugosus; and
   0-50 dosages of magnolia officinalis.

3. The pharmaceutical composition of claim 2, further comprising:
   1-50 dosages of cinnamon;
   1-50 dosages of radix scutellariae;
   1-50 dosages of radix codonopsis;
   0-50 dosages of radix rehmanniae preparata; and
   0-50 dosages of Yam Rhizome.

4. The pharmaceutical composition of claim 3, further comprising:
   0-50 dosages of monkshood;
   0-50 dosages of caulis spatholobi; and
   1-50 dosages of rhizome sparganii.

5. The pharmaceutical composition of claim 3, further comprising:
   1-50 dosages of radix achyranthis bidentatae;
   1-50 dosages of rhizoma alismatis;
   1-50 dosages of polyporus;
   1-50 dosages of angelica pubescens;
   0-50 dosages of herba taxilli; and
   1-50 dosages of asarum.

6. The pharmaceutical composition of claim 5, further comprising:
   1-50 dosages of ligusticum wallichii and
   1-50 dosages of radix angelicae dahuricae.

7. Application of pharmaceutical composition of claim 1 in medical drugs, health food, health products, animal drugs, and animal feed.

* * * * *